United States Patent
De Jonge et al.

(10) Patent No.: US 9,857,320 B2
(45) Date of Patent: Jan. 2, 2018

(54) DEVICE AND METHOD FOR THE STOICHIOMETRIC ANALYSIS OF SAMPLES

(71) Applicant: LEIBNIZ-INSTITUT FUER NEUE MATERIALIEN GEMEINNUETZIGE GMBH, Saarbruecken (DE)

(72) Inventors: Niels De Jonge, St. Ingbert (DE); Diana B. Peckys, St. Ingbert (DE)

(73) Assignee: LEIBNIZ-INSTITUT FUER NEUE MATERIALIEN GEMEINNUETZIGE GESELLSCHAFT MIT BESCHRAENKTER HAFTUNG, Saarbruecken (DE)

( * ) Notice: Subject to any disclaimer, the term of this patent is extended or adjusted under 35 U.S.C. 154(b) by 0 days.

(21) Appl. No.: 15/314,141

(22) PCT Filed: Jun. 18, 2015

(86) PCT No.: PCT/DE2015/100245
§ 371 (c)(1),
(2) Date: Nov. 28, 2016

(87) PCT Pub. No.: WO2015/197050
PCT Pub. Date: Dec. 30, 2015

(65) Prior Publication Data
US 2017/0205363 A1    Jul. 20, 2017

(30) Foreign Application Priority Data
Jun. 24, 2014 (DE) .................. 10 2014 108 825

(51) Int. Cl.
*G01N 23/00* (2006.01)
*G01N 23/225* (2006.01)
*H01J 37/20* (2006.01)

(52) U.S. Cl.
CPC .......... *G01N 23/2251* (2013.01); *H01J 37/20* (2013.01); *G01N 2223/307* (2013.01); *G01N 2223/418* (2013.01); *G01N 2223/612* (2013.01)

(58) Field of Classification Search
CPC ......... G01N 23/2251; G01N 2223/612; G01N 2223/418; G01N 2223/307; H01J 37/20
(Continued)

(56) References Cited

U.S. PATENT DOCUMENTS

| 4,990,776 A | 2/1991 | Fushimi et al. |
| 5,811,804 A | 9/1998 | Van Blitterswijk et al. |

(Continued)

FOREIGN PATENT DOCUMENTS

| WO | 2004020453 A1 | 3/2004 |
| WO | 2010120238 A1 | 10/2010 |

(Continued)

OTHER PUBLICATIONS

Diana B Peckys et al: "Liquid Scanning Transmission Electron Microscopy: Imaging Protein Complexes in their Native Environment in Whole Eukaryotic Cells" Microscopy and Mircoanalysis, Springer, New York, US, vol. 20, No. 2, Apr. 1, 2014, pp. 346-365.
(Continued)

*Primary Examiner* — Michael Maskell
(74) *Attorney, Agent, or Firm* — Collard & Roe, P.C.

(57) ABSTRACT

The present invention relates to a device and a method for the stoichiometric analysis of samples.
In order to study the spatial distribution of different proteins in the plasma membrane of a complete cell within a short time frame, a device and a method are proposed for the stoichiometric analysis of samples.
The object is established by means of a device for the stoichiometric analysis of samples, said device comprising
(Continued)

a) a sample processing device comprising a sample holder for holding the sample, means for setting the temperature, means for adding and removing fluids (including gases) and at least one fluid reservoir,
b) an electron microscope with a detector, and
c) a computer-controlled process control system for controlling the means for setting the temperature and the means for adding and removing fluids (including gases), a computer-controlled and automated imaging device that captures images by means of the electron microscope, a unit that stores the captured images and an image analysis unit controlled by the computer.

19 Claims, 3 Drawing Sheets

(58) Field of Classification Search
USPC .................................. 250/306, 307, 310, 311
See application file for complete search history.

(56) References Cited

U.S. PATENT DOCUMENTS

| | | | |
|---|---|---|---|
| 8,604,429 B2* | 12/2013 | Yaguchi | H01J 37/20 250/306 |
| 2007/0249064 A1 | 10/2007 | De La Fuente et al. | |
| 2011/0284745 A1 | 11/2011 | Nishiyama et al. | |
| 2012/0025103 A1 | 2/2012 | Deshmukh et al. | |
| 2012/0120226 A1* | 5/2012 | de Jonge | G01N 23/2204 348/80 |
| 2012/0182548 A1* | 7/2012 | Harb | G01N 21/05 356/246 |
| 2012/0292505 A1* | 11/2012 | Damiano | H01J 37/20 250/307 |
| 2013/0200262 A1 | 8/2013 | Kruit et al. | |
| 2014/0246583 A1* | 9/2014 | Ominami | H01J 37/16 250/307 |
| 2015/0034822 A1 | 2/2015 | Reinhorn et al. | |
| 2015/0214001 A1* | 7/2015 | Buijsse | H01J 37/20 250/307 |
| 2015/0293084 A1 | 10/2015 | Del Pino Gonzalez De La Higuera et al. | |

FOREIGN PATENT DOCUMENTS

| | | |
|---|---|---|
| WO | 2014007624 A1 | 1/2014 |
| WO | 2014016465 A1 | 1/2014 |

OTHER PUBLICATIONS

Elisabeth A Ring et al: "Microfluidic System for Transmission Electron Microscopy", Microscopy and Vlicroanalysis, Springer, New York, US, vol. 16, No. 5, Oct. 1, 2010, pp. 622-629.
International Search Report of PCT/DE2015/100245, dated Oct. 13, 2015.
International Search Report of PCT/DE2015100097 dated Jul. 10, 2015.
A. C. Zonnevylle et al., "Integration of a high-NA light microscope in a scanning electron microscope," Journal of Microscopy, vol. 252, Issue 1, 2013, pp. 58-70.
Nalan Liv et al., "Simultaneous Correlative Scanning Electron and High-NA Fluorescence Microscopy," PLOS ONE, Feb. 2013, vol. 8, Issue 2, e55707, total of 10 pages.
Kyoung, Lee et al: "Rapid Detection of Intracellular Nanopartides by Electron Microscopy", Journal of Analytical Science & Technology, vol. 1, No. 1, Jan. 1, 2010, pp. 71-73.
Watanabe, Shigeki et al: "Protein localization in electron micrographs using fluorescence nanoscopy", Nature Methods, vol. 8, No. 1, Jan. 2011, pp. 1-18.
International Search Report of PCT/DE2015/100238 dated Oct. 27, 2015.

* cited by examiner

DEVICE AND METHOD FOR THE STOICHIOMETRIC ANALYSIS OF SAMPLES

CROSS REFERENCE TO RELATED APPLICATIONS

This application is the National Stage of PCT/DE2015/100245 filed on Jun. 18, 2015, which claims priority under 35 U.S.C. §119 of German Application No. 10 2014 108 825.5 filed on Jun. 24, 2014, the disclosure of which is incorporated by reference. The international application under PCT article 21(2) was not published in English.

The present invention relates to a device and a method for the stoichiometric analysis of samples.

One of the next great scientific challenges following the decoding of human-genome DNA is to investigate and understand the function of over ten thousand proteins that control cellular functions. Many of the important cellular processes are controlled via the dynamic formation and dissociation of proteins in protein complexes. Understanding cellular function at protein level is thus of crucial importance for biomedical research, for example research aimed at developing new active substances against diseases such as cancer and AIDS. Proteomics is the research field that investigates protein interaction in cells. Investigating the functions of proteins is highly complex because proteins have nanoscale dimensions and are present in huge numbers within a cell.

Up until now, most of the currently available knowledge has been obtained via indirect biochemical methods, for example by extracting certain proteins from a large number of cells and then separating protein complexes by gel electrophoresis, for example. This procedure provides averaged information on very large numbers, typically several thousands, of cells. However, it does not provide vital information pertaining to individual cells, small groups of cells or to certain areas within cells. Information pertaining above all to small populations, however, is important for the generation of knowledge relating to cellular functions and for drug development. It may happen, for example, that a certain cancer drug is effective against most cancer cells but not against a small population of mutated cancer cells. A small population of cells, for example, may thus survive when this drug is administered therapeutically. It is therefore deemed highly important for new methods to be developed with which individual proteins in individual cells can be investigated.

The use of light-microscopy methods enables areas in which certain proteins are located to be visualized by means of specific markers. Use is made, for example, of fluorescence tags produced by genetic modification of cells. These express, for example, green fluorescent protein to which a specific protein is linked.

The fact that spatial resolution is limited in light microscopy, preventing direct visualisation of whether certain proteins form a complex or not, is a drawback.

Certain indirect light-microscopy techniques, such as Förster Resonance Energy Transfer (FRET), do exist and are used to detect complex formation in proteins. However, FRET only allows conclusions as to the presence of neighbouring molecules. Accurate spatial resolution of these molecules is not possible, nor is it possible to distinguish between the components of largish protein complexes.

Electron microscopy is the method of choice for investigating nanoscale dimensions. However, where conventional electron microscopy is used to image cellular ultrastructures, thin sections of cells, either embedded in plastic or frozen, are required, which means the cells do not remain intact. This is problematic for researching membrane proteins, which are responsible for many important cellular functions, because the planar cell membrane is served when the section is cut and thereafter can only be investigated as a two-dimensional line structure. A further drawback is that the investigation of thin sections is very time consuming. For example, investigating a whole cell in the form of a large number of sections would involve several weeks' work.

The object of the invention is thus to provide a device and a method for use in proteonics, which enables the spatial distribution of different proteins to be investigated in complete cells, each of which can be investigated separately, within a short time.

The object is established by means of a device for the stoichiometric analysis of samples, said device comprising
  a) a sample processing device comprising a sample holder for holding the sample, means for setting the temperature, means for adding and removing fluids and at least one fluid reservoir,
  b) an electron microscope with a detector, and
  c) a computer-controlled process control system for controlling the means for setting the temperature and the means for adding and removing fluids, a computer-controlled and automated imaging device that captures images by means of the electron microscope, a unit that stores the captured images and an image analysis unit controlled by the computer.

In this context, fluids include both gases and liquids.

The sample processing setup, or cell processing setup, consists of various components. Provision is made for the sample to be available, in immobilized form, in a well (depression) of a microwell plate. The sample is preferably immobilized on a sample holder. The sample holder may be a membrane. Various fluids (liquids and/or gases) may be supplied to the sample, which may be disposed in a well, by way of a means for adding fluids, for example a pipette tip. The means for adding fluids is connected via flexible tubing to a fluid-mixing chamber. The invention provides for the means for adding fluids to be connected with a manipulator for the three dimensions, x, y, z, so that the means for adding fluids is able to supply fluid to all the wells. The fluid may be withdrawn from the at least one fluid reservoir of the fluid-mixing chamber by means of a syringe or pump unit and then supplied to the at least one sample. It is envisaged that a plurality of fluid reservoirs, which have different volumes and contain different fluids, be available. The liquid, which may be a buffer, a cell culture medium or the like, may be removed (after a specified time) by a fluid-removing means connected via flexible tubing to a container or to a further measuring system, for example a chemical analysis facility, or, for example, by a further pump unit. The invention also provides for the means for removing fluids to be connected to a manipulator for the three dimensions, x, y, z, so that the means for removing fluids is able to remove fluid from all the samples, which may be disposed in wells.

High-resolution images may be captured by means of an electron microscope either during sample preparation or as soon as sample preparation has been completed by the sample processing setup. The sample holder and the electron microscope are suitably positioned relative to one another for this purpose.

It is conceivable in this context that the images be captured by a device for correlative scanning transmission electron microscopy and light microscopy.

The third part of the device for the stoichiometric analysis of samples comprises a computer and driver unit, which includes both electrical and mechanical components. The computer controls sample processing in an automated manner. Once the samples have been processed, the computer switches the sample-processing settings to electron-microscopy performance and records the electron-microscopy images. Automated software ensures that the desired areas of the samples are imaged and that information is obtained from the tags on the samples. The invention also provides for the computer to contain automated-data-analysis software, so that the relevant information pertaining to the samples is obtained automatically.

According to the invention, the sample holder is disposed in a well.

In this context, it is conceivable that the sample holder be disposed on the bottom of the well or, by means of spacers placed beneath the sample holder, be disposed within the well but above the bottom thereof.

It is also within the scope of the invention for the sample holder to be configured as a thin, electron-permeable membrane. This is to advantage for investigations with the electron microscope.

The invention furthermore provides for the samples to be applied to the sample holder in a liquid and to be covered with a lid that has an electron-permeable window.

It is within the scope of the invention for the sample processing device to have a three-dimensional, movable microscope stage.

An embodiment of the invention provides for the samples to be investigated by means of a scanning electron microscope (SEM).

According to another embodiment of the invention, the samples are investigated by means of a transmission electron microscope (TEM).

The invention also provides for micrographing by means of a device for scanning transmission electron microscopy (STEM), where a STEM detector sensitive to atomic number, referred to as z-contrast, is used. Thanks to the STEM detector, the tags, or markers, provide a greater contrast than the surrounding cell material. This detector may be installed either in the SEM or the TEM.

The possibility of establishing a vacuum in the well is also within the scope of the invention.

According to the invention, furthermore, the samples are dried and exposed to a vacuum so as to permit investigation by electron microscopy.

The invention also provides for the samples to be cooled down to a few degrees Celsius and exposed to a weak vacuum of approx. 10 mbar. In this context, the vacuum is set precisely such that, first, excess liquid vaporises and that subsequently a thin film of liquid, whose thickness is in the nanometer range, is maintained above the sample, so that, for example, cells may be investigated in liquid.

The invention also provides for the samples to be investigated directly in liquid by means of electron microscopy, the vacuum in the electron microscope being separated from the sample chamber by a thin membrane. The thickness of the thin membrane is in the nanometer range.

According to another embodiment of the invention, the samples are also investigated by means of a light microscope, for example a fluorescence microscope. In this case, the sample is transferred from the one to the other microscope or the two microscopes are integrated in one device.

An embodiment of the invention provides for the sample holder to contain marks that are identifiable both in a light-microscopy image and in an electron-microscopy image. This embodiment is expedient in that it enables the site information obtained via the two microscopy methods to be correlated. The mark may, for example, be a silicon edge fabricated to an accuracy of approx. 100 nm.

An embodiment of the invention provides for the device to include a light microscope that comprises a photo-optical lens with a cavity.

According to this embodiment, the detection device combines efficient STEM-microscopy detection of materials with high atomic numbers, for example specific nanoparticle markers in a sample, such as a cell, contained in a liquid with simultaneous light microscopy, for example via fluorescence contrast of fluorescent protein markers in cells or via scatter contrast of the cell material. The use of a device of this kind permits extremely efficient detection, with the maximum possible resolution, of materials with high atomic numbers in the sample as well as complete time-correlative light microscopy. For example, the exact positions of quantum-dot (QD)-labeled proteins, for example, may be compared with the occurrence, in fluorescence-microcopy images, of fluorescence with wavelengths typical of the QD type. This information may be used to identify the cells or cellular regions containing a certain protein.

It is also to advantage here that the STEM detector of the electron microscope is positioned in the cavity of the photo-optical lens.

In a further advantageous embodiment, the cavity has, at the sample end, a small-diameter opening followed by a electron drift chamber at the bottom end of which the STEM detector is located.

"Bottom" refers here to an electron beam direction from top to bottom. Arbitrary beam directions are possible depending on how the device is set up. This means that the opening is located at the lens end which is nearer the sample holder. Following on from the opening is a (conical) electron drift chamber, which widens out in the downward direction. The STEM detector of the scanning transmission electron microscope is located at the bottom end of the electron drift chamber.

The signal from the STEM detector can be transmitted to the outside at the side of the lens.

The possibility of establishing a vacuum in the electron drift chamber is also within the scope of the invention.

For purposes of micrographing by means of a device for correlative scanning transmission electron microscopy and light microscopy, provision may also be made for an electron-beam source to be located on the other side of the sample holder from the STEM detector.

The detection device may also have a lens to which a light source and light-optical detection means are connected.

The lens with the integrated STEM detector may be installed in different kinds of electron microscopes, e.g. in an Environmental Scanning Electron Microscope (ESEM) with typical electron energy of 10 to 30 keV or in a high-resolution STEM with typical electron energy of 200 keV.

It is advantageous if the detection device for correlative scanning transmission electron microscopy and light microscopy has one or more other light-optical beam paths for purposes of detection or illumination.

It is also possible, for purposes of micrographing by means of a device for correlative scanning transmission electron microscopy and light microscopy, for the light source to be fitted at the side of the STEM detector, the focus of the light beam to overlap with the electron beam and the light-optical detection path to overlap with the illumination beam.

It would also be possible, for purposes of micrographing by means of a device for correlative scanning transmission electron microscopy and light microscopy, to use a device in which the STEM detector is positioned between the optical lens and the sample. In the same way, it is possible for the STEM detector to be movable in the area between the optical lens and the sample.

Provision is also made for the use of an additional detector, e.g. a secondary electron detector or a backscatter detector. The detection of x-ray signals is equally conceivable.

According to the invention, furthermore, the samples are biological cells, preferably eukaryotic cells.

However, it is just as conceivable that the samples are biological molecules, nanoparticles, polymers or ceramic or metallic microstructures.

It is to advantage if the thin, electron-permeable membrane is supported by a microchip and/or a grid.

In this context, the invention provides for the thin, electron-permeable membrane to consist of silicon nitride or silicon oxide, or to be coated with carbon.

The object of the invention is also established by means of a method for the stoichiometric analysis of samples, using a device according to claim 1 and comprising the steps of:
 a) Applying the sample to the sample holder,
 b) Processing the sample with the sample processing device,
 c) Capturing a series of electron-microscopy images of various parts of the sample and visualizing the positions of nanoparticle-tagged proteins,
 d) Storing the individual electron-microscopy images in the image-storing unit,
 e) Evaluating the electron-microscopy images.

According to the method of the invention, a scanning electron microscope (SEM), a transmission electron microscope (TEM) or a scanning transmission electron microscope (STEM) is used as electron microscope. The use of a STEM detector is also within the scope of the invention.

It is likewise conceivable that a light microscope for capturing light-microscopy images be used in addition to the electron, microscope. The light-microscopy images may be captured additionally at any desired point in time after sample processing.

The method is explained below, using cells as examples of samples. It goes without saying, however, that the method may also be used to analyse other samples.

The cells are first applied, in a liquid environment that keeps them alive, to the carrier membrane, to which they adhere. The cells are then incubated with specific markers for a selected group of proteins, enabling, for example, a protein in the cell membrane of a eukaryotic cell to be marked. The markers may consist of nanoparticles, e.g. gold nanoparticles, but also nanoparticles of other materials. If different nanoparticle materials are used, these will differ in their electron densities. The nanoparticles may also differ in shape. They may be, for example, spherical, elliptical, rod-shaped or cubic. The use of fluorescent nanoparticles is also conceivable. The linker between the protein and the nanoparticle may, for example, be a protein linker such as streptavidin biotin or it may consist of a short, carbon-based molecule such as a lipid. Provision is made for the linker to have, at the other end from the nanoparticle, a binding site for the protein. It is furthermore envisaged that the linkers be sufficiently small, approx. in the 5-10 nm range, so as to enable a plurality of markers to bind specifically to the various components of a protein complex. Use may be made, for example, of an antibody fragment. An alternative, in the event that a certain receptor is to be investigated, is to use a ligand for a receptor protein. It is also possible to use a small chemical molecule for binding specifically to a protein. This small chemical molecule consists of a short peptide sequence with a maximum of 60 amino acids or of a short RNA or DNA sequence made up of a maximum of 70 nucleotides.

A possible application for the specific protein marker may, by way of example, be its use for detection of the HER2 protein, of new cancer drugs, and as a possible candidate for diagnosing cancer. HER2 is of particular importance for breast cancer, as it is overexpressed in approximately one third of all malignant breast tumours and this correlates significantly with a reduced survival period. A peptide may be used in this instance, which is able to bind specifically to HER2 and which is related to the domain of staphylococcal protein A (SPA), which has around 1-13 substitution mutations.

A further possibility consists in cloning a streptavidin-binding region into the target protein. Other equivalent alternatives naturally exist, too, and fall within the scope of the invention. Incubation with the markers may be performed simultaneously or sequentially. It is also within the framework of the invention that the ligands or antibodies bind to the protein first and then to the subsequently added marker, which contains nanoparticles. The cells may be fixed, for example with glutaraldehyde. However, it is also conceivable that the cells are not fixed.

It is furthermore conceivable that a marker for specific protein labeling comprises two units, the first unit comprising a small molecule for specifically binding to a protein and at least one chemically coupled molecule for binding to the second unit, and the second unit comprising a surface-modified nanoparticle with a surface coating comprising at least one molecule for binding to the first unit.

In the next procedural step, the cells are investigated by means of the electron microscopy. The electron microscope generates images/data pertaining to the sites of the specific markers in a given region of the cell. These images/data are stored in a memory. Electron microscopy is a familiar technique and is not explained further here. The invention also provides for the recording of data/images pertaining to numerous regions in a plurality of cells. The information on the the sites and sizes of these regions is then stored. It is preferable, according to the invention, for electron microscopy to be carried out in fully automated manner. If the sample is always of a similar kind, a standard method may be programmed.

Electron microscopes generate two-dimensional images. Three-dimensional information may be obtained optionally, for example by capturing images of the sample at different angles of inclination.

The invention also provides for images to be recorded with a light microscope in order to generate general images of cells, which reflect the cells' viability, or to visualize cellular regions with fluorescent markers. This information may serve, for example, to find out in which cells or cellular regions, and to what extent there in each case, a certain protein occurs. This enables populations in which a protein is expressed differently to be selected and identified.

It is additionally possible to conduct a time-resolved investigation of a living cell by means of light and/or fluorescence microscopy, thereby enabling cellular processes to be researched dynamically. As soon as a given process has reached a given stage, a specified phase of the labeling or fixation procedure is initiated so that the marker information correlates temporally with a cellular process. The exact time of labeling following administration of an active agent, e.g. a carcinostatic drug, may also be determined in this way.

According to the invention, an automated analysis of the marker positions is performed during the procedure. The positions of the markers may be determined automatically using suitable software.

The invention also provides for the software to first of all filter out the images/data pertaining to noise and background variations. A threshold value is then set and the pixels that exceed it are examined to determine which signal levels and shapes belong to which nanoparticles.

The images are then analysed for the existence of different nanoparticles. The software distinguishes between the different shapes and signal levels and decides whether the pixels reflect a certain marker. The invention also provides for the software to recognize markers of different sizes. Different marker shapes are also recognized, for example spherical, elliptical, rod-like and cubic shapes. The software can also recognize and differentiate between markers with different electron densities, as these have different signal levels. As soon as a marker of a certain type is recognized, its mean pixel position is determined and stored.

This data analysis process may be used for two-dimensional and three-dimensional images. A database containing information on marker type and position can be built up in this way, with different marker types reflecting different proteins. This database also contains information pertaining to the site and size of the region in which the image was captured.

Next, the collected information is sorted and partially overlapping areas of images are removed. This analysis is performed for all the desired areas of the cells in a well. If necessary, the data from other wells is also analysed.

The resulting database contains information pertaining to the sites of the selected groups of proteins in a selected set of cellular regions and to a selected set of cells.

An embodiment of the invention provides for specific markers, in particular nanoparticles that bind specifically to proteins, to be supplied to the sample in step b) of the method. Fluorescent markers may also be used.

If two of more different protein species are being investigated, these may be labeled with different markers that are mutually distinguishable. This enables different forms of the "epidermal growth factor receptor" (EGFR) family, for example, to be detected simultaneously. Examples of markers include nanoparticles of different sizes (commercially available nanoparticles include those with diameters of 1.4, 5, 10 or 20 nm) or shapes, for example spherical, ellipsoidal rod-shaped, cubic, etc. It is also possible to use nanoparticles made of different materials, e.g. nanoparticles of Au, PbSe, CdSe/ZnS or Pt. CdSe/ZnS nanoparticles, in particular, are advantageous for investigating cells with correlative fluorescence microscopy and electron microscopy. However, nanoparticles of Ni or Fe may also be used in combination with imaging methods.

The device and the method of this invention are not limited to the investigation of labeled proteins in cells. They may also be used for various other applications. It is possible to investigate any other sample requiring automated chemical processing and electron microscopy. Experiments in which bacteria or biological compounds, such as protein complexes, DNA or viruses, are exposed to different chemical conditions are examples of applications for the device and method of the invention. Protein crystallization may also be investigated rapidly, in a series of experiments, with the device and the method. A further application is the investigation of the self-assembly of nanoparticles having certain coatings as a function of the properties of the surrounding liquid, or the investigation of microstructures formed by polymers under different chemical conditions. The investigation of metal pieces is also conceivable, for example, the investigation of corrosion formation in steel under different conditions. It is also possible to analyse low-density biopsy material. Various other materials may also be investigated.

The invention is explained below by reference to drawings.

The drawing in

Figure 1:
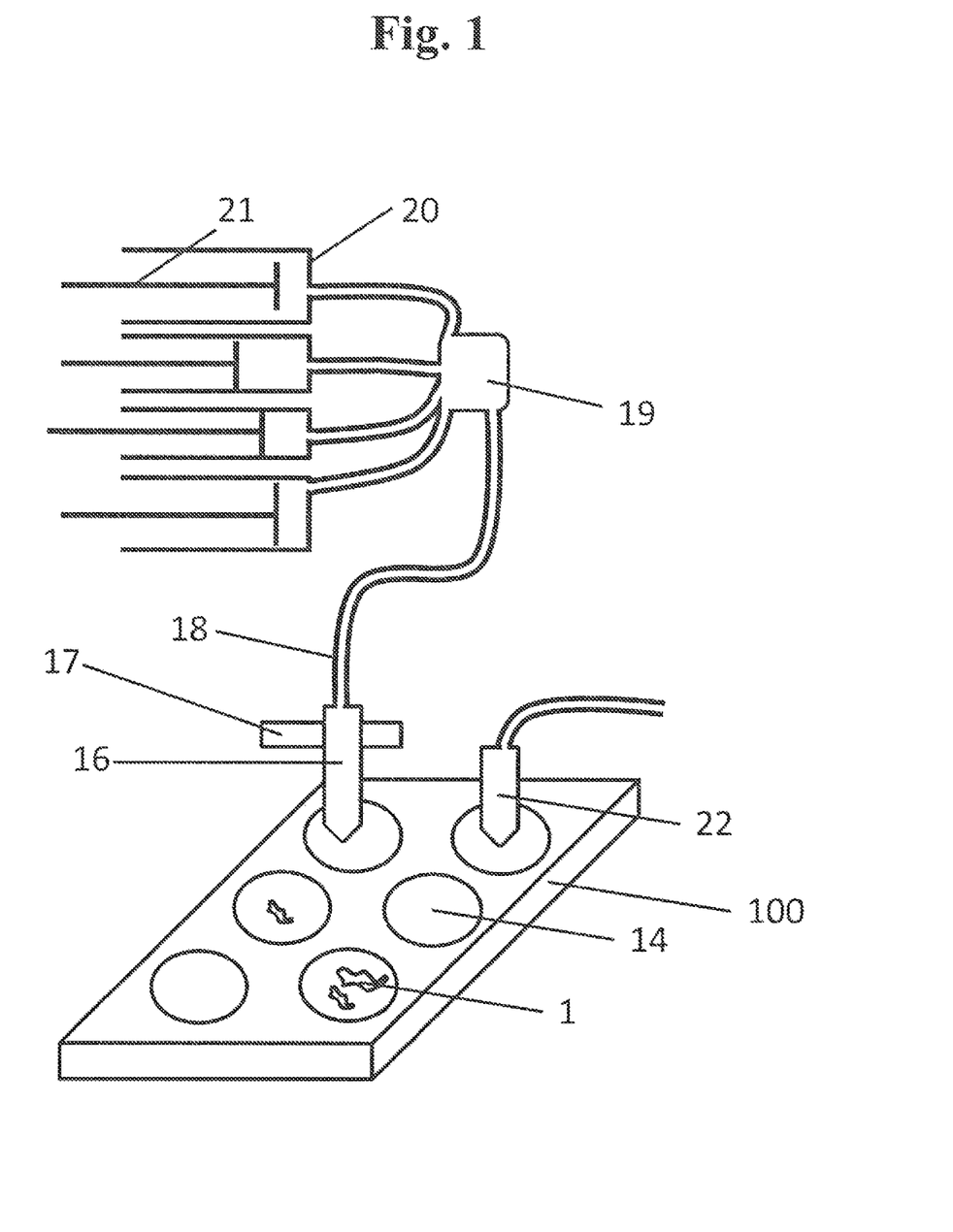
FIG. 1 shows a schematic view of the components of the device for the stoichiometric analysis of samples.

FIG. 1 shows a schematic view of some of the possible components of a cell processing device. Provision is made for the cells (1) to be contained in a liquid and preferably to be immobilized in a well (depression) (14) of a plate (100) suitable for cell culture. The cells are preferably immobilized on a sample holder (15) (see FIG. 2). The sample holder may be a membrane. FIG. 1 shows a cell-culture plate (100) with 6 wells. However, it is also conceivable that the cells be cultivated in 24-well or 96-well plates or any other plates of standard cell-culture format. By way of example, the cells (1) adhere to the bottom of the well (14). Various fluids (liquids and/or gases) may be transferred from the at least one fluid reservoir (20) to the well by means of a pipette tip (16) connected to a fluid-mixing chamber (19) via flexible tubing (18). The pipette tip (16) is connected to a manipulator (17) for the three dimensions, x, y and z, so that the pipette tip (16) is able to supply fluid to all the wells. The fluid may be withdrawn from the at least one fluid reservoir (20) of the fluid-mixing chamber (19) by means of a syringe or a pump unit (21) and then supplied to the at least one well (14). Provision is made for a plurality of fluid reservoirs (20), which have different volumes and contain different fluids, to be available. The liquid, which may be a buffer, a cell culture medium or the like, may be removed (after a specified time) by means of a second pipette tip (22) connected via flexible tubing (18) to a container or to a further measuring system, for example an HPLC facility. The liquid is removed by a further pump device, for example. According to the invention, moreover, the second pipette tip (22) is connected to a further manipulator for the three dimensions, x, y and z. The second pipette tip (22) is thus able to remove fluid from all the wells (depressions).

Figure 2:
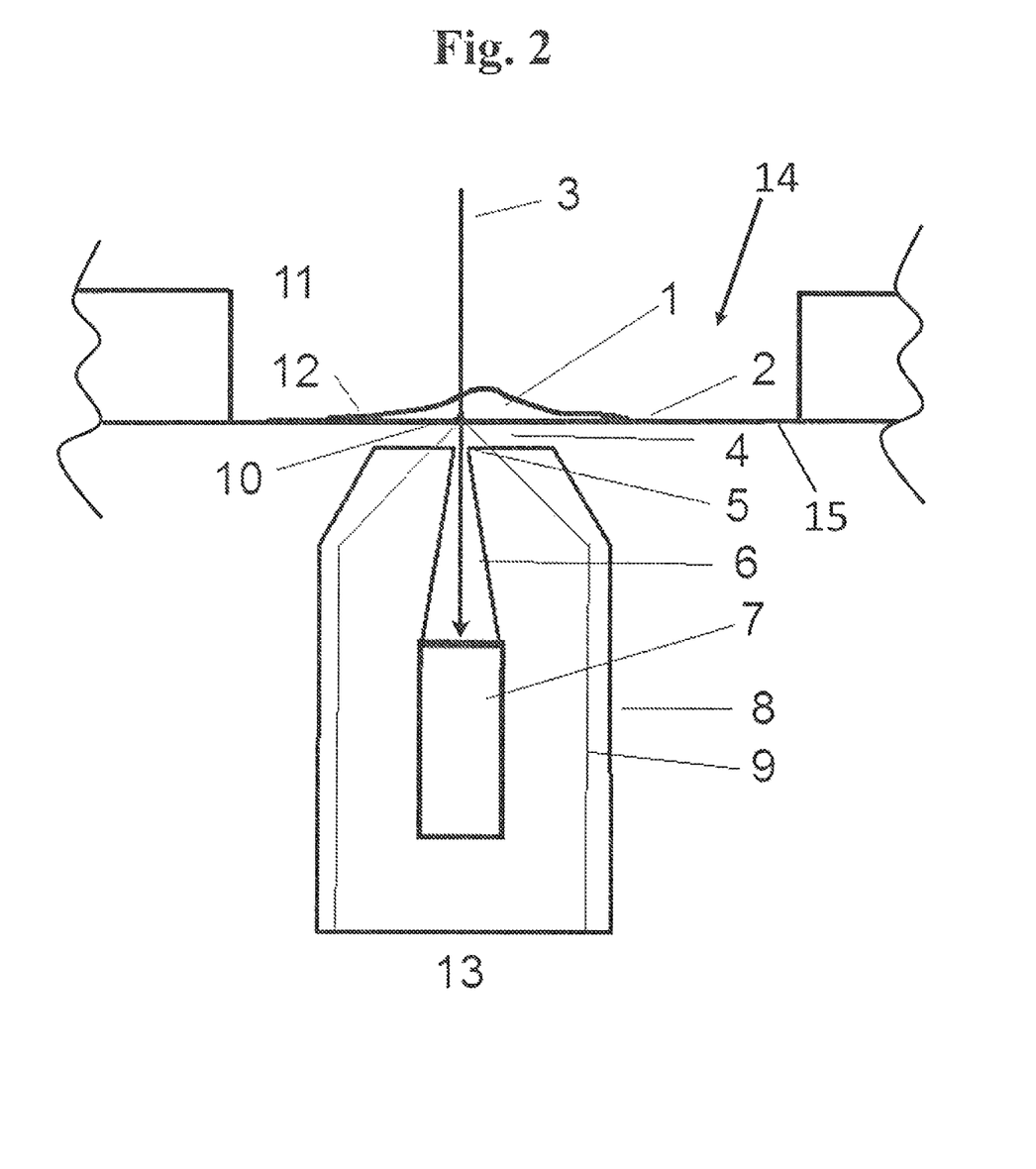
FIG. 2 shows a schematic view of the detection device for correlative scanning transmission electron microscopy and light microscopy.

FIG. 2 shows a detection device for correlative scanning transmission electron microscopy and light microscopy. A sample (1), for example a eukaryotic cell (1), is in place, within a well (14), on a sample holder (15), for example on a thin, electron-permeable membrane (2). The membrane (2) is connected to the specimen holder (15). The sample (1) is imaged with an electron beam (3), the sample (1) typically being scanned with an electron beam (3). Transmitted electrons propagate through the membrane (2), across a gap (4), into an electron drift chamber (6) within a cavity with a small opening (5), to the STEM detector (7). The electron drift chamber (6) and the STEM detector (7) are located in a cavity in the photo-optical lens (8). The lens (8) focuses a broad light beam (9) onto the sample (1) at a focal point (10). The sample (1) and the electron drift chamber (6) are surrounded by a vacuum (11). A thin layer of liquid (12) covers the sample (1). The photo-optical detection means and the light source are located in the area (13) beneath the lens (8).

The procedure according to the invention is as follows:

A sample (1) in a liquid, for example a eukaryotic cell, is in place on a thin membrane (2). The membrane (2) consists of lightweight materials of low atomic number, for example carbon, silicon oxide or silicon nitride, enabling an electron beam (3) of sufficient energy, for example 30 keV or 200 keV, to permeate said membrane (2).

The membrane (2) is supported by a carrier, e.g. a silicon microchip or a thin material. The carrier is disposed on a sample holder having means to move in the x, y and z directions. The electron beam (3) is configured such that the beam runs from the top end to the bottom end of the microscope and through the sample (1). The electron beam may, of course, run in another direction instead of from top to bottom, for example from bottom to top or from left to right.

A special optical lens (8) is in place beneath the membrane (2). The optical path is configured such that the light passes through the lens (8) and is focused onto the sample, while reflected or fluorescent light is collected by the same lens (8) and routed to the detector, for example by using an optical filter cube consisting of dichroic mirrors. The light beam converges toward the sample (1) with a semi-aperture angle of, for example, 0.75 rad, said angle being defined by the numerical aperture of the lens (8). A high-resolution air or vacuum lens provides 100-fold magnification in the case of a numerical aperture of 1.0 and a working distance of 0.15 mm. The lens (8) focuses the light beam (9) onto the sample (1). At the other end of the lens (8) the light beam (9) is broad, with a diameter of, for example, 9 mm. The lens (8) has a conical cavity which is located along the optical axis of the lens (8) and serves as electron drift chamber (6). The dimensions of the conical cavity are suited to the beam path used for STEM detection, with typical semi-aperture angles of 0.050 to 0.20 rad. At the top end of the lens (8), directly beneath the specimen (1), the diameter of the cavity is, for example, 0.060 mm. It decreases by 0.20 rad over a distance of 0.15 mm. The cavity extends through the lens (8) at an angle of 0.2 rad. At the bottom end of a lens (8) of 10 mm length the diameter of the cavity is thus 4.0 mm. The STEM detector (7) is positioned at the widest point of the cavity.

Although the presence of the cavity limits the optical path through the lens (8), it only reduces the overall amount of light passing through the lens (8). The lens (8) is still able to focus the light beam onto the sample (1), collect light from the sample and project a magnified image of the illuminated area onto a position-sensitive light detector for purposes of light microscopy. A confocal optical system may be used as an alternative. Alternatively, it is also possible to use a plurality of additional photo-optical beam paths for purposes of detection or illumination.

The STEM detector consists of a cylinder of scintillator material, having a diameter of, for example, 4.0 mm, for converting electrons into light pulses. The scintillator is coupled with a sensitive light detector, for example a multiplier phototube. This tube is connected to the side of the lens. For this purpose, the scintillator has a connection surface at the side of the optical lens. The outside is provided with reflective, slightly stepped material so as to prevent light from the photo-optical beam path from being coupled into the STEM detector (7). The STEM detector (7) may also consist of a small microchip with a CCD detector. The central disc of the STEM detector (7), with an appropriate half-angle of 50 mrad, is decoupled from detection, for example blocked, or the signal from this area is used as secondary detection signal. The STEM detector (7) accordingly registers signals from transmitted electrons with half-angles of 50 mrad to 0.20 rad. The signal is referred to as the dark field signal.

Figure 3:
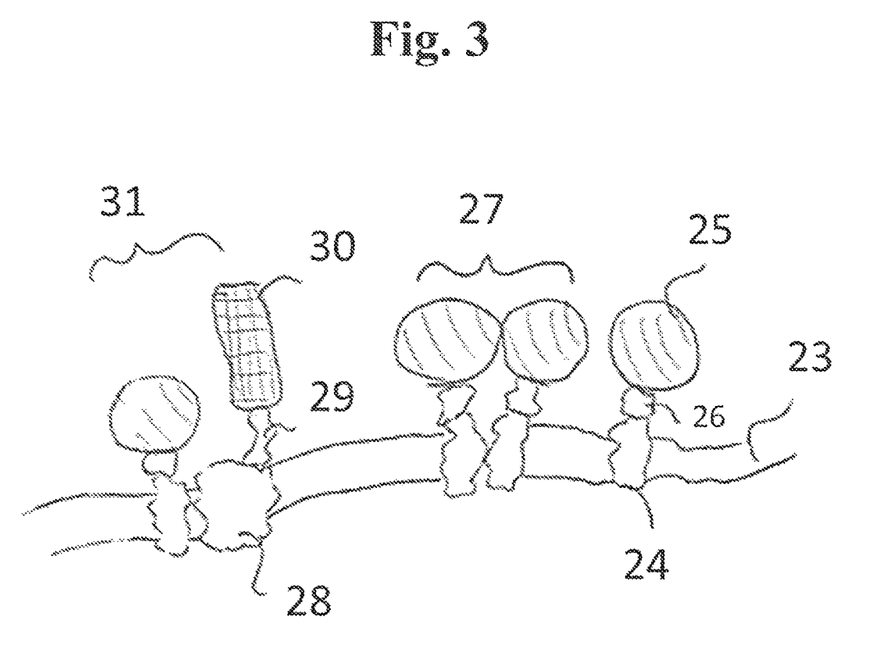
FIG. 3 shows a schematic view of a cellular plasma membrane.

FIG. 3 shows a schematic view of a cellular plasma membrane consisting of a double lipid layer (23) with membrane proteins (24). The upper side is the exterior side of the cell. An antibody fragment (26) is bound to the membrane protein and a gold nanoparticle (25) adheres to the antibody fragment. The membrane also has a pair of the same protein (dimer) with two gold nanoparticles (27). Another kind of membrane protein (28) is bound to another antibody (29) and is labeled with a gold particle of a different shape (30). The pair (31) made up of two different proteins is detectable on account of the proximity of the two different markers.

The invention claimed is:

1. Device for the stoichiometric analysis of samples (16, 17, 18, 19, 21, 22), comprising
   a) a sample processing device comprising a sample holder (15) for holding the sample (1), means for setting the temperature, means for adding and removing fluids (16, 17, 18, 19, 21, 22) and at least one fluid reservoir (20),
   b) an electron microscope with a detector, and
   c) a computer-controlled process control system for controlling the means for setting the temperature and the means for adding and removing fluids (16, 17, 18, 19, 21, 22), a computer-controlled and automated imaging device that captures images by means of the electron microscope, a unit that stores the captured images and an image analysis unit controlled by the computer,
   wherein the detector (7) is a STEM (scanning transmission electron microscopy) detector,
   wherein the device includes a light microscope that comprises a photo-optical lens (8) with a cavity (5), and
   wherein the STEM detector (7) is positioned in the cavity (5) of the photo-optical lens (8).

2. Device according to claim 1 for the stoichiometric analysis of samples (1), wherein the sample holder (15) is disposed in a well (14).

3. Device according to claim 1 for the stoichiometric analysis of samples (1), wherein the sample holder (15) is configured as a thin, electron-permeable membrane (2).

4. Device according to claim 2 for the stoichiometric analysis of samples (1), wherein the samples (1) are applied to the sample holder in a liquid (12) and are covered with a lid that has an electron-permeable window.

5. Device according to claim 1 for the stoichiometric analysis of samples (1), wherein the sample processing device has a three-dimensional, movable microscope stage.

6. Device according to claim 1 for the stoichiometric analysis of samples (1), wherein the electron microscope is a scanning electron microscope (SEM).

7. Device according to claim 1 for the stoichiometric analysis of samples (1), wherein the electron microscope is a transmission electron microscope (TEM).

8. Device according to claim 1 for the stoichiometric analysis of samples (1), wherein the device includes a light microscope.

9. Device according to claim 2 for the stoichiometric analysis of samples (1), wherein a vacuum can be established in the well (14).

10. Device according to claim 1 for the stoichiometric analysis of samples (1), wherein the samples (1) are biological cells.

11. Device according to claim 1 for the stoichiometric analysis of samples (1), wherein the samples (1) are biological molecules, nanoparticles, polymers or ceramic or metallic microstructures.

12. Device according to claim 3 for the stoichiometric analysis of samples (1), wherein the thin, electron-permeable membrane (2) is supported by a microchip and/or a grid.

13. Device according to claim 3 for the stoichiometric analysis of samples (1), wherein the thin, electron-permeable membrane (2) comprises silicon nitride or silicon oxide or is coated with carbon.

14. Method for the stoichiometric analysis of samples (1) using a device according to claim 1, comprising the steps of:
   a) Applying the sample to the sample holder,
   b) Processing the sample with the sample processing device,
   c) Capturing a series of electron-microscopy images,
   d) Storing the individual electron-microscopy images in the image-storing unit,
   e) Evaluating the electron-microscopy images.

15. Method according to claim 14 for the stoichiometric analysis of samples (1), wherein light-microscopy images are captured in addition.

16. Method according to claim 14 for the stoichiometric analysis of samples (1), wherein one or more of the steps b) to e) of the method are repeated.

17. Method according to claim 14 for the stoichiometric analysis of samples (1), wherein specific markers, in particular nanoparticles (25; 27; 30) that bind specifically to proteins, are supplied to the sample in step b) of the method.

18. Device for the stoichiometric analysis of samples (16, 17, 18, 19, 21, 22), comprising
   a) a sample processing device comprising a sample holder (15) for holding the sample (1), means for setting the temperature, means for adding and removing fluids (16, 17, 18, 19, 21, 22) and at least one fluid reservoir (20),
   b) an electron microscope with a detector, and
   c) a computer-controlled process control system for controlling the means for setting the temperature and the means for adding and removing fluids (16, 17, 18, 19, 21, 22), a computer-controlled and automated imaging device that captures images by means of the electron microscope, a unit that stores the captured images and an image analysis unit controlled by the computer,
   wherein the detector (7) is a STEM (scanning transmission electron microscopy) detector,
   wherein the device includes a light microscope that comprises a photo-optical lens (8) with a cavity (5), and
   wherein the cavity (5) has, at the sample end, a small-diameter opening followed by an electron drift chamber (6) at the lower end of which the STEM detector (7) is located.

19. Device according to claim 18 for the stoichiometric analysis of samples (1), wherein a vacuum can be established in the electron drift chamber (6).

* * * * *